United States Patent [19]

Farng et al.

[11] Patent Number: 5,324,441
[45] Date of Patent: Jun. 28, 1994

[54] PHOSPHORODITHIOATE-DERIVED PYRROLIDINONE ADDUCTS AS MULTIFUNCTIONAL ANTIWEAR/ANTIOXIDANT ADDITIVES

[75] Inventors: Liehpao O. Farng, Lawrenceville; Andrew G. Horodysky, Cherry Hill; Ronald J. Poole, Mullica Hill, all of N.J.

[73] Assignee: Mobil Oil Corporation, Fairfax, Va.

[21] Appl. No.: 985,044

[22] Filed: Dec. 3, 1992

[51] Int. Cl.$^5$ .......................... C10M 137/10
[52] U.S. Cl. .................. 252/32.7 E; 252/32.7 R; 252/46.7
[58] Field of Search .............. 252/32.7 R, 32.7 E, 252/46.7; 548/413; 558/166, 169, 170

[56] References Cited

U.S. PATENT DOCUMENTS

| | | | |
|---|---|---|---|
| 2,624,707 | 1/1953 | Pritzker et al. | 548/413 |
| 2,644,002 | 6/1953 | Hoeberg | 252/46.7 |
| 2,706,194 | 4/1955 | Morris et al. | 548/413 |
| 2,895,912 | 12/1958 | Pohlemann | 548/413 |
| 2,959,610 | 11/1960 | Young et al. | 548/413 |
| 3,658,840 | 4/1972 | Oswald | 558/166 |

Primary Examiner—Prince Willis, Jr.
Assistant Examiner—Alan D. Diamond
Attorney, Agent, or Firm—Alexander J. McKillop; Malcolm D. Keen; Charles A. Malone

[57] ABSTRACT

Vinyl pyrrolidinone capped phosphorodithioates have been found to be effective multifunctional antiwear/antioxidant additives for lubricants.

11 Claims, No Drawings

PHOSPHORODITHIOATE-DERIVED PYRROLIDINONE ADDUCTS AS MULTIFUNCTIONAL ANTIWEAR/ANTIOXIDANT ADDITIVES

BACKGROUND OF THE INVENTION

1. Field of the Invention

This application is directed to vinyl pyrrolidinone phosphorodithioates as multifunctional additives and lubricant compositions containing same.

2. Description of Related Art

The use of phosphorodithioate compositions, especially the corresponding salts of phosphorodithioates, such as zinc dialkylphosphorodithioates (commonly known as zinc dithiophosphates) have found widespread commercial use for several decades in engine oils as multifunctional antiwear, peroxide decomposing, and bearing corrosion inhibiting additives.

1-Vinyl-2-pyrrolidinone (also known as N-Vinyl Pyrrolidone) is an essential monomeric building block for the preparation of many useful specialty polymers and copolymers. This heterocyclic compound imparts superb solubility, stability, and alkalinity, and therefore, can provide many potentially beneficial characteristics, such as anti-corrosion, anti-oxidation properties to lubricants when it is built into the additive structures.

It has now been found that the use of these phosphorodithioate-derived pyrrolidinones provides exceptional antioxidant and antiwear/EP activity with potential corrosion inhibiting, anti-fatigue and high temperature stabilizing properties.

BRIEF SUMMARY OF THE INVENTION

It is an object of this invention to provide a novel method of preparing phosphorodithioate-derived pyrrolidinone adducts suitable for use as multifunctional additives in lubricant compositions. More specifically vinyl pyrrolidinone capped phosphorodithioates, for example, have been prepared by the method in accordance with the invention and found to be excellent antiwear/antioxidant lubricant additives. Therefore, it is a further object of this invention to provide lubricant compositions having improved antiwear/antioxidant characteristics.

Lubricant compositions containing small additive concentrations of O,O-dihydrocarbyl phosphorodithioate-derived pyrrolidinones possess excellent antiwear properties coupled with very good antioxidant and extreme pressure load carrying activities. Both the phosphorodithioate moiety and the pyrrolidinone moiety are believed to provide the basis for the synergistic antiwear activity. The phosphorodithioate group is also believed to contribute significant antioxidant characteristics to these novel additives.

All of these beneficial properties are believed to be enhanced as a result of this novel internal synergism. This unique internal synergism concept is believed to be applicable to similar structures containing (a) dithiophosphate groups, (b) pyrrolidinone groups within the same molecule. The products of this patent application show good stability and compatibility when used in the presence of other commonly used additives in lubricant compositions.

DESCRIPTION OF PREFERRED EMBODIMENTS

As noted hereinabove, the phosphorodithioate-derived pyrrolidinones described herein provide exceptional antioxidant and antiwear/EP activity. They also possess potential corrosion inhibiting and anti-fatigue and high temperature stabilizing properties. They may be generally prepared as described hereinbelow.

O,O-Dialkyl phosphorodithioic acids (made by the reaction of alcohols, phenols, diols, hydrocarboxyesters or similar OH containing species with phosphorus pentasulfide) or O,O-diaryl phosphorodithioic acids (made by the reaction of phenols with phosphorus pentasulfide) were reacted with vinyl pyrrolidones to form phosphorodithioate-derived pyrrolidones as generally described below:

$$R_1OH + R_2OH + P_2S_5 \rightarrow (R_1O)(R_2O)PSSH \quad (1)$$

where $R_1$, $R_2$ are $C_3$ to $C_{30}$ hydrocarbyl.

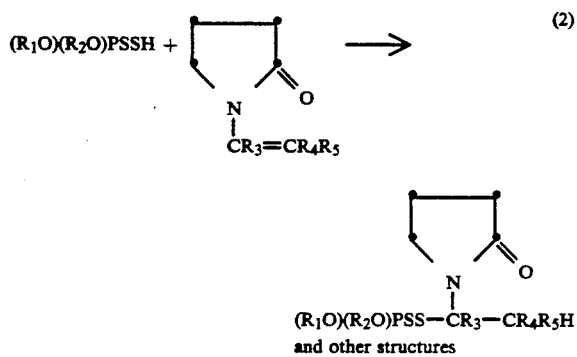

and other structures where $R_3$, $R_4$, $R_5$ are hydrogen, or $C_1$ to $C_{60}$ hydrocarbyl.

Any suitable $C_3$ or $C_{30}$ hydrocarbyl alcohol or hydrocarbyl-substituted phenol may be used to make the corresponding phosphorodithioic acids. These acids may also be obtained from convenient commercial sources. Highly useful are propyl alcohols and substituted propyl alcohols such as 2-methyl-1-propanol.

If a solvent is desired, any suitable hydrocarbon solvent such as toluene or the xylenes may be used.

Conditions for the above reactions may vary widely depending upon specific reactants, the presence or absence of a solvent and the like. Any suitable set of reaction conditions known to the art may be used. Generally stoichiometric quantities of reactants are used. However, equimolar, more than molar or less than molar amounts may be used. Accordingly, an excess of one reagent or another can be used. Molar quantities, less than molar quantities or more than molar quantities of phosphorodithioates or vinyl pyrrolidones can be used. However, exact stoichiometry is preferred. The reaction temperature may vary from ambient to about 250° C. or reflux, the pressure may vary from ambient or to about 100 psi in autogenous and the molar ratio of reactants preferably varies from about 0.1 moles to about 10 moles of one reactant versus 1.0 mole of the other reactant preferably in reaction (1) the molar ratio of alcohol or phenol to $P_2S_5$ is from about 3:1 to about 5:1 and in reaction (2) the molar ratio of the resultant phosphorodithioic acid to pyrrolidone varies from 1:5 to about 5:1 or is equimolar.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt. % based on the total weight of the composition can be used. Preferably, the concentration is from 0.1 to about 3 wt. %.

The additives have the ability to improve the above noted characteristics of various oleagenous materials such as hydrocarbyl lubricating media which may comprise liquid oils in the form of either a mineral oil or a synthetic oil, or a mixture of mineral and synthetic oils or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. These oils may preferably have viscosity indexes ranging to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for foaming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

It is to be understood, however, that the compositions contemplated herein can also contain other materials. For example, corrosion inhibitors, antiwear/extreme pressure agents, low or high temperature properties modifiers, friction modifiers, VI improvers and the like can be used as exemplified respectively by metallic phenates sulfonates, polymeric succinimides, non-metallic or metallic phosphorodithioates and the like. These materials may constitute up to about 20% weight based on the weight of the total composition. They do not detract from the value of the compositions of this invention, rather the materials serve to impart their customary properties to the particular compositions in which they are incorporated.

The following examples are meant to be illustrations only and are not to be considered limitations.

EXAMPLE 1

N-Vinyl-2-Pyrrolidone Capped Di-(2-Ethylhexyl) Phosphorodithioic Acid

Approximately 354.3 g of di-(2-ethylhexyl) phosphorodithioic acid (commercially obtained from ICI America Company) were charged into a 1 liter stirred reactor equipped with a condenser and a thermometer. It was heated at 70° C. while 111.1 g of 1-vinyl-2-pyrrolidinone (1.0 mole) was added dropwise over one hour. After all of the vinyl pyrrolidone reactant was introduced, the temperature reached 79° C. due to the reaction exotherm. It was then reacted at 70°–79° C. for two additional hours and the final product changed its color from dark greenish to light yellowish. It weighed approximately 464 g, and contained 6.21% of phosphorus (theory 6.66%) and 2.8% of nitrogen (theory 3.0%).

EXAMPLE 2

N-Vinyl-2-Pyrrolidone Capped Di-(2-Methylpropyl) Phosphorodithioic Acid

Into a four-necked flask equipped with a stirrer, condenser, dropping funnel and thermometer were added 608 g (8.2 moles) of 2-methyl-1-propanol and the contents were heated to 60° C. At that temperature, 444.5 g (2.0 mole) of phosphorus pentasulfide was added portion-wise over a 3-hour period with agitation. After all of the sulfide reactant was introduced, the temperature was raised to 65° C. and held for 3 hours. The evolution of hydrogen sulfide gas was trapped by a caustic scrubber which indicates a substantially complete reaction. The reaction was then allowed to cool to ambient temperature under a nitrogen blanket and the solution was filtered through diatomaceous earth to produce a greenish fluid (927 g) as the desired phosphorodithioic acid.

A portion of this phosphorodithioic acid (121 g) was further reacted with equimolar N-vinyl-2-pyrrolidone (55.5 g) following the generalized procedure as described in Example 1. At the end of the reaction, the product mixture changed its color to light yellowish.

The products were blended into mineral oils and evaluated for antioxidant performance by Catalytic Oxidation Test at 325° F. for 40 hours (Table 1); Catalytic Oxidation Test at 325° F. for 72 hours (Table 2), Catalytic Oxidation Test at 375° F. for 24 hours (Table 3).

TABLE 1

| | Catalytic Oxidation Test (40 hours at 325° F.) | | | |
|---|---|---|---|---|
| Item | Additive Conc. (wt %) | Change In Acid Number Δ TAN | Percent Change In Viscosity % Δ KV | Sludge | Lead Loss (mg) |
| Base Oil (200 second, solvent | — | 13.02 | 112.5 | Heavy | 122 |

TABLE 1-continued

Catalytic Oxidation Test
(40 hours at 325° F.)

| Item | Additive Conc. (wt %) | Change In Acid Number Δ TAN | Percent Change In Viscosity % Δ KV | Sludge | Lead Loss (mg) |
|---|---|---|---|---|---|
| refined, paraffinic neutral, mineral oil) | | | | | |
| Example 2 in above base oil | 1.0 | 1.40 | 34.7 | Heavy | 0.3 |

TABLE 2

Catalytic Oxidation Test
(72 hours at 325° F.)

| Item | Additive Conc. (wt %) | Change In Acid Number Δ TAN | Percent Change In Viscosity % Δ KV | Sludge | Lead Loss (mg) |
|---|---|---|---|---|---|
| Base Oil (200 second, solvent refined, paraffinic neutral, mineral oil) | — | 9.60 | 118.9 | Heavy | 418 |
| Example 2 in above base oil | 1.0 | 1.97 | 39.7 | Heavy | 12.6 |

TABLE 3

Catalytic Oxidation Test
(24 hours at 375° F.)

| Item | Additive Conc. (wt %) | Change In Acid Number Δ TAN | Percent Change In Viscosity % Δ KV | Sludge |
|---|---|---|---|---|
| Base Oil (200 second, solvent refined, paraffinic neutral, mineral oil) | — | 6.53 | 177.9 | Medium |
| Example 1 in above base oil | 1.0 | 3.25 | 90.0 | Light |

The oxidation tests consist basically of bubbling a stream of air through a volume of the lubricant at the rate of 5 liters per hour respectively at 325° F. for 40 hours or 72 hours and at 375° F. for 24 hours; see U.S. Pat. No. 3,682,980 incorporated herein by reference for further details.

As shown above, the products of this invention show very good antioxidant activity as evidenced by control of increase in acidity and viscosity.

The dithiophosphate derived pyrrolidinone was also evaluated for antiwear performance using the Four-Ball Test (Table 4).

TABLE 4

Four-Ball Test
(60 kg load, 1000 rpm, 30 min.)

| Item | Wear Scar Diameter (mm) 200° F. | 300° F. |
|---|---|---|
| Base oil (80% solvent paraffinic bright, 20% solvent paraffinic neutral mineral oil) | 1.908 | 1.953 |

TABLE 4-continued

Four-Ball Test
(60 kg load, 1000 rpm, 30 min.)

| Item | Wear Scar Diameter (mm) 200° F. | 300° F. |
|---|---|---|
| 1% of Example 1 in above base oil | 0.496 | 0.621 |

The results clearly show good antiwear activity by this adduct.

The use of additive concentrations of N-vinyl pyrrolidone capped dithiophosphates in premium quality automotive and industrial lubricants will significantly enhance the stability, reduce the wear and extend the service life. These additives uniquely combine the beneficial effects of a phosphorodithioate group and pyrrolidone group within the same composition deriving synergistic performance improvements.

What is claimed is:

1. An improved automobile or industrial lubricant composition comprising a major proportion of an oil of lubricating viscosity or grease prepared therefrom and a minor proportion of a multifunctional antiwear/antioxidant additive product of reaction prepared by (a) reacting an O,O-dihydrocarbyl phosphorodithiioic acid with a vinyl pyrrolidone to form phosphorodithioate-derived pyrrolidones as described below:

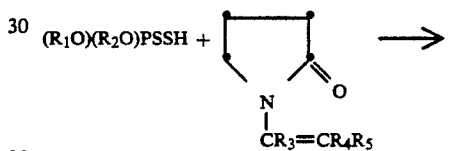

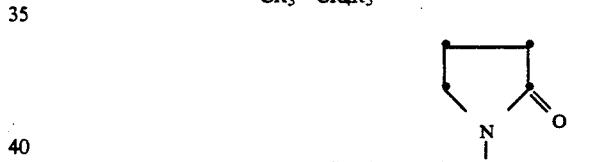

where $R_1$ and $R_2$ are $C_3$ to about $C_{30}$ hydrocarbyl and where $R_3$, $R_4$ and $R_5$ are hydrogen or $C_1$ to about $C_{60}$ hydrocarbyl and wherein the reaction is carried out at temperatures varying from ambient to about 250° C. under pressures varying from ambient to about 100 psi or is autogenous for a time sufficient to obtain the desired additive product of reaction and where the reaction is carried out in molar ratios of reactants which vary from equimolar to more than equimolar to less than equimolar.

2. The composition of claim 1 wherein the reactants are di-(2-ethylhexyl)phosphorodithioic acid and 1-vinyl-2-pyrrolidinone.

3. The composition of claim 1 wherein the phosphorodithioic acid is first formed by reacting a $C_3$ to about a $C_{30}$ alcohol or a $C_6$ to about a $C_{30}$ alkylated phenol with phosphorus pentasulfide in a molar ratio of alcohol or phenol to phosphorus pentasulfide of about 3 to 1 to about 5 to 1 and thereafter reacting in equimolar ratios the resultant phosphorodithioic acid with N-vinyl-2-pyrrolidone.

4. The composition of claim 3 wherein said alcohol is 2-methyl-1-propanol.

5. The composition of claim 1 wherein the oil of lubricating viscosity is selected from the group consisting of (1) mineral oils, (2) synthetic oils, (3) or mixtures of mineral and synthetic oils or is (4) a grease prepared from any one of (1), (2) or (3).

6. The composition of claim 5 wherein the lubricant contains from about 0.001 to about 10 wt % based on the total weight of the composition of the additive product of reaction.

7. The composition of claim 5 wherein the oil is a mineral oil.

8. The composition of claim 5 wherein the oil is a synthetic oil.

9. The composition of claim 5 wherein the oil is a mixture of mineral and synthetic oils.

10. The composition of claim 5 wherein the lubricant is a grease.

11. The composition of claim 1 containing in addition to said oil of lubricating viscosity and said additive from 0 to about 20 wt % of an additive package comprising viscosity index improvers, friction modifiers, antiwear-/extreme pressure agents and anticorrosion agents.

* * * * *